United States Patent [19]
Wright et al.

[11] Patent Number: 5,911,036
[45] Date of Patent: Jun. 8, 1999

[54] HEAD CURSOR CONTROL INTERFACE FOR AN AUTOMATED ENDOSCOPE SYSTEM FOR OPTIMAL POSITIONING

[75] Inventors: James Wright, Santa Barbara; Hamid Wasti, Sacramento; Darrin R. Uecker, Santa Barbara, all of Calif.

[73] Assignee: Computer Motion, Inc., Goleta, Calif.

[21] Appl. No.: 08/904,047

[22] Filed: Jul. 31, 1997

Related U.S. Application Data

[63] Continuation of application No. 08/529,095, Sep. 15, 1995, Pat. No. 5,825,982.

[51] Int. Cl.$^6$ .............................. A61B 17/00; A61B 1/00
[52] U.S. Cl. ........................................ 395/94; 364/413.13
[58] Field of Search ......................... 395/94; 364/413.13

[56] References Cited

U.S. PATENT DOCUMENTS

| | | | |
|---|---|---|---|
| 4,863,133 | 9/1989 | Bonnell | 248/278 |
| 5,572,999 | 11/1996 | Funda et al. | 128/653.1 |

Primary Examiner—George B. Davis
Attorney, Agent, or Firm—Blakely Sokoloff Taylor & Zafman

[57] ABSTRACT

An interface that allows a surgeon to remotely control surgical devices and conditions of an operation room. The surgeon views a video image that is displayed by a monitor. The monitor may be coupled to a video device such as a laparoscopic camera that is attached to the end of an endoscope. Static graphic images and a dynamic graphic cursor are overlayed onto the video image. The graphic cursor has a pixel location on the monitor which corresponds to a spatial location of a pointer signal. The pointer signal is transmitted by a transmitter worn on the head of the surgeon. The pointer signal may be a laser which is directed to a screen that is located adjacent to a detection camera. The surgeon may move the graphic cursor relative to the video image by tilting his head and varying the spatial location of the pointer signal. The interface may have a controller which generates output signals in response to the movement of the pointer signal. The output signals may move a robotic arm which controls the position of the endoscope. The controller may also generate command signals when the graphic cursor is moved into a static graphic image. The command may vary a condition of the operating room such as the position of the operating table.

6 Claims, 4 Drawing Sheets

5,911,036

HEAD CURSOR CONTROL INTERFACE FOR AN AUTOMATED ENDOSCOPE SYSTEM FOR OPTIMAL POSITIONING

This application is a Continuation of application Ser. No. 08/529,095, filed Sep. 15, 1995, U.S. Pat. No. 5,825,982.

BACKGROUND OF THE INVENTION

1. Field of the Invention

The present invention relates to a graphical user interface that can be remotely controlled by a surgeon to control various devices and conditions of an operating room.

2. Description of Related Art

To reduce the invasiveness of surgery, endoscopes are commonly utilized to view the internal organs of a patient. One end of the endoscope contains a lens which is inserted into the patient through a small incision of the skin. The lens focuses an image that is transmitted by fiber optic cable to a camera located at the opposite end of the endoscope. The camera is coupled to a monitor that displays a video image of the patient.

The endoscope can be used in conjunction with another surgical instrument that is inserted into the patient. An assistant typically holds the endoscope while the surgeon manipulates the surgical instrument. The assistant moves the endoscope in response to instructions from the surgeon. Any mis-communication between the surgeon and the assistant may result in an error in the movement of the endoscope, thereby requiring the surgeon to repeat the instruction. Additionally, holding the endoscope for a significant amount of time may cause the assistant to become fatigued.

U.S. application Ser. No. 07/927,801 discloses a robotic arm that holds and moves an endoscope in response to commands from the surgeon. The commands are provided through a hand controller or a foot pedal. The controller and pedal require coordinated movements which may detract the surgeon from the surgical procedure. It would be desirable to provide an interface that manipulates a robotically controlled surgical device while requiring minimal physical coordination by the surgeon. Additionally, it would be desirable to provide a single interface that allows the surgeon to control a number of devices such as an operating table, laparoscopic camera, laser tool, etc.

SUMMARY OF THE INVENTION

The present invention is an interface that allows a surgeon to remotely control surgical devices and conditions of an operation room. The surgeon views a video image that is displayed by a monitor. The monitor may be coupled to a video device such as a laparoscopic camera that is attached to the end of an endoscope. Static graphic images and a dynamic graphic cursor are overlayed onto the video image. The graphic cursor has a pixel location on the monitor which corresponds to a spatial location of a pointer signal. The pointer signal is transmitted by a transmitter worn on the head of the surgeon. The pointer signal may be a laser which is directed to a screen that is located adjacent to a detection camera. The surgeon may move the graphic cursor relative to the video image by tilting his head and varying the spatial location of the pointer signal. The interface may have a controller which generates output signals in response to the movement of the pointer signal. The output signals may move a robotic arm which controls the position of the endoscope. The controller may also generate command signals when the graphic cursor is moved into a static graphic image. The command may vary a condition of the operating room such as the position of the operating table.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
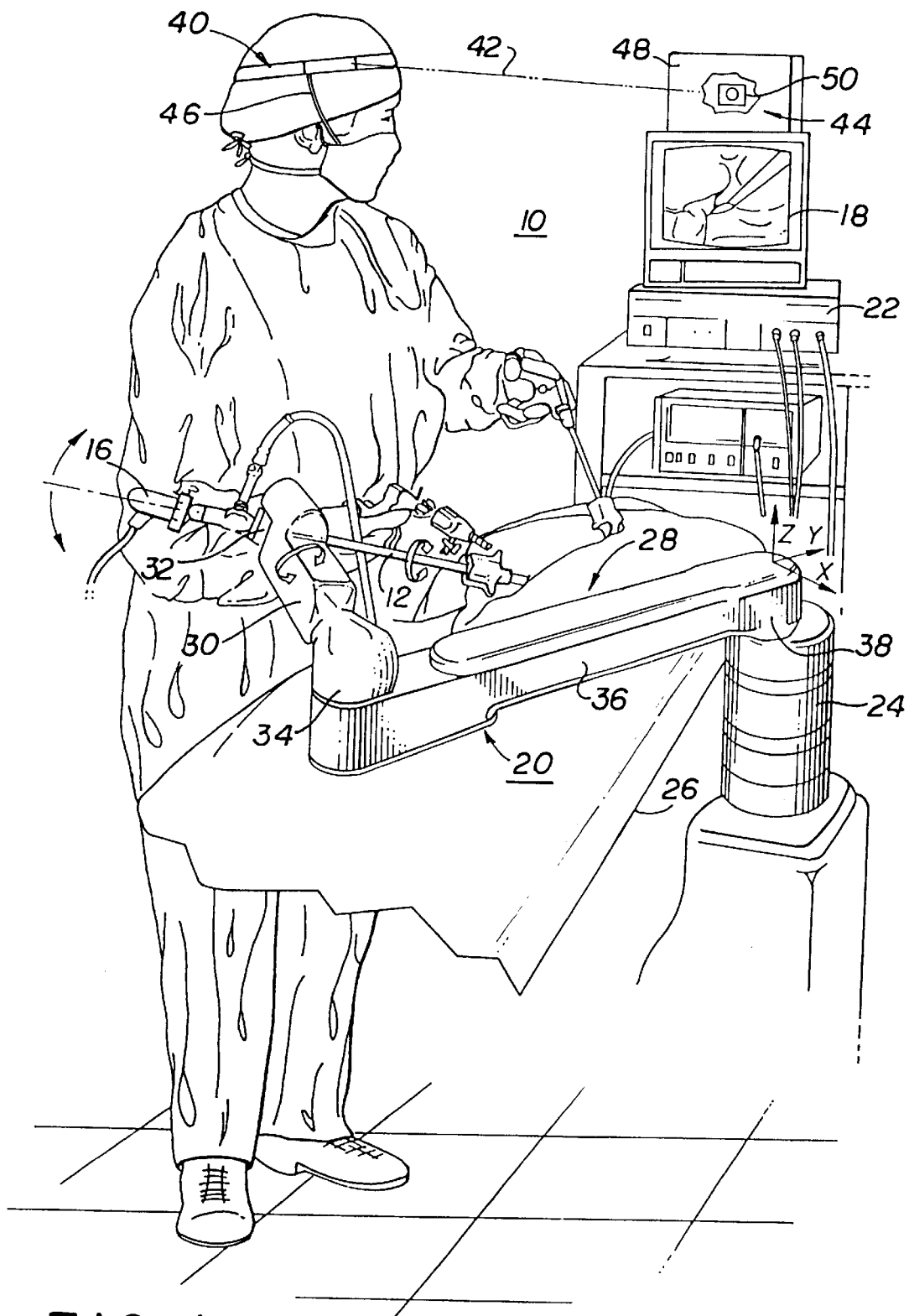
FIG. 1 is a perspective view of a robotic system that controls an endoscope.

Referring to the drawings more particularly by reference numbers, FIG. 1 is a robotic system 10 that controls a surgical instrument 12. The surgical instrument 12 is typically an endoscope that is inserted into a patient. The tip of the endoscope typically has a lens(es) that focuses an image of the patient. The endoscope 12 may also have fiber optic cable that transmits the image to a camera 16 located at the end of the scope. The camera 16 is typically a charge coupled device (CCD). The camera 16 is coupled to a monitor 18 which displays the image.

The instrument 12 is moved by a robotic arm assembly 20 that is coupled to a computer 22. In the preferred embodiment the robotic assembly 20 has a linear actuator 24 that is mounted to a surgical table 26. The linear actuator 24 moves a linkage arm assembly 28 in a linear manner relative to the table 26. The linear actuator 24 defines an origin of a fixed first coordinate system that has a first x axis, a first y axis and a first z axis.

The linkage arm assembly 28 contains a first linkage arm 30 attached to an end effector 32. The first linkage arm 30 is mounted to a first rotary actuator 34 which can rotate the arm. The first rotary actuator 34 is attached to a second linkage arm 36. The second linkage arm 36 is mounted to a second rotary actuator 38 that can rotate the arms. The rotary actuator 38 is attached to the output shaft of the linear actuator 24.

Figure 2:
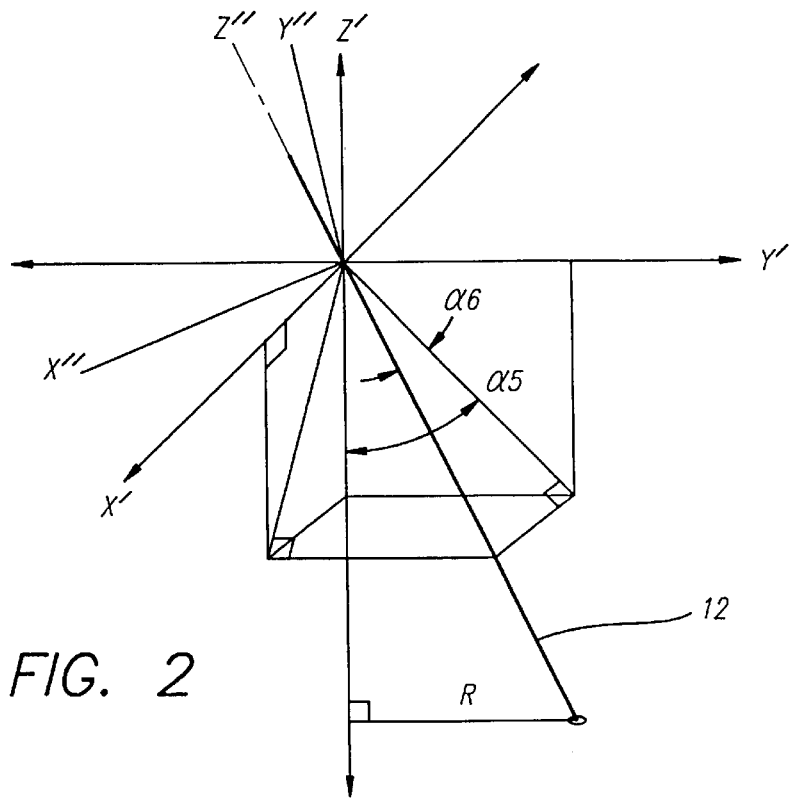
FIG. 2 is a schematic of an endoscope within two different coordinate systems.

The end effector 32 is typically coupled to a pair of passive joints (not shown) that allow rotation of the instrument as indicated by the arrows in FIG. 1. The end effector 32 may also have a worm gear (not shown) that rotates the endoscope about the longitudinal axis of the instrument. As shown in FIG. 2, the junction of the instrument 12 and the end effector 32 define the origin of a second coordinate system which has a second x axis (x'), a second y axis (y') and a second z axis (z'). The junction of the end effector 32 and the instrument 12 also define a third coordinate system which has a third x axis (x"), a third y axis (y") and a third z axis (z"). The z" axis is always parallel with the longitudinal axis of the instrument 12. The actuators receive input signals from the computer 22 to control the movement of the robotic arm assembly 20.

Referring to FIG. 1, the surgeon wears a transmitter unit 40 that transmits a pointer signal 42 which is received by a receiver unit 44. The transmitter unit 40 is preferably a laser pointer which emits a laser beam 42. The laser pointer may have a blow switch 46 that allows the surgeon to turn the laser on and off by blowing or drawing in the air of a tube located adjacent to the surgeons mouth. The transmitter 40 may be a laser switch sold by Point Source, Inc. of Germantown, Ohio. Although a laser transmitter is shown and described, the transmitter may be an acoustic or electromagnetic device that generates a wave that is detected by an appropriate detector(s). It being understood that any system that can detect a physical movement of the surgeon is encompassed by the present invention.

The receiver unit 42 preferably includes a screen 48 that is in the field of view of a camera 50. The laser beam 42 creates an illuminated dot on the screen 48 which is then detected by the camera 50. The camera 50 is preferably a charged coupled device (CCD). When the surgeon moves his head, the pointer signal 42 moves to a new spatial location on the screen 48. The surgeon can therefore control the position of the illuminated dot by tilting his head.

Figure 3:
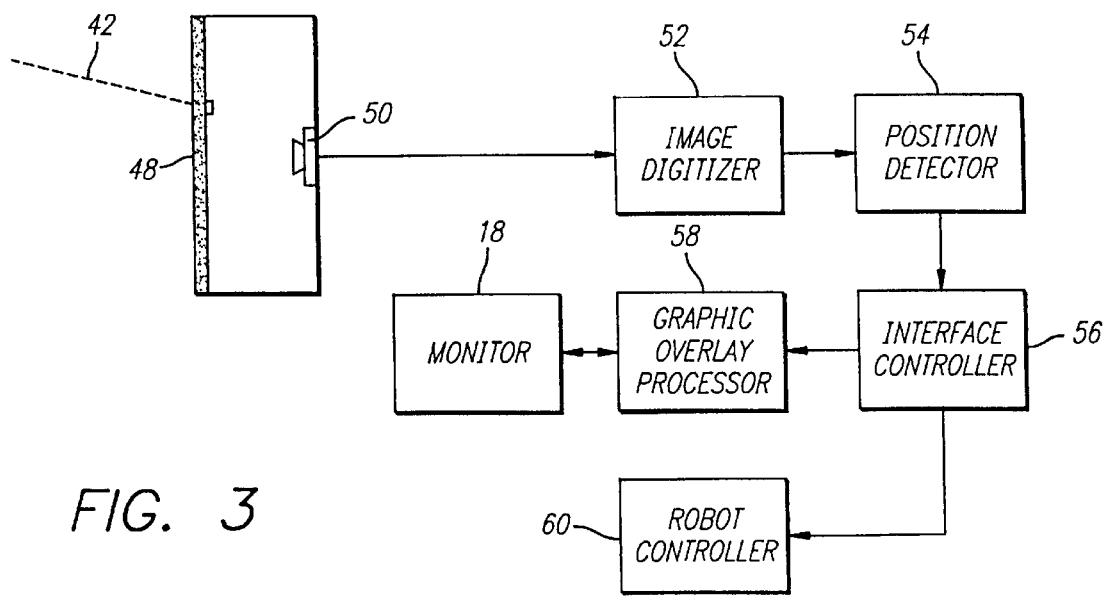
FIG. 3 is a schematic of a head cursor interface.

As shown in FIG. 3, the CCD camera 50 is coupled to an image digitizer 52 which digitizes the images provided by the camera 50. The digitizer 52 provides digitally based values that correspond to the light intensity detected by each pixel of the camera 50. The digitizer 52 is coupled to a position detector 54 which detects the spatial location of the pointer signal 42 relative to the screen 48. The detector 54 first compares the intensity values of each pixel with a threshold value. The detector 54 provides an associated value of 1 for each pixel that has an intensity which exceeds the threshold value, and a value of 0 for each pixel which is below the threshold value. The threshold value is selected to correspond to the intensity of an illuminated dot created by the laser beam 42 striking the screen 50. The threshold value is preferably large enough to filter out background light.

After each pixel is assigned a 1 or 0 value, the x and y spatial coordinates of the pointer signal 42 relative to the screen 48 is computed by determining the center of mass of the pixels which have an assigned value of 1 in accordance with the following equations.

$$Mx = \frac{\sum_{i-n, j-m} x_i \cdot O(i, j)}{\sum_{i-n, j-m} O(i, j)} \quad My = \frac{\sum_{i-n, j-m} y_j \cdot O(i, j)}{\sum_{i-n, j-m} O(i, j)}$$

where;
Mx=the x coordinate of the center of mass.
My=the y coordinate of the center of mass.
O(i,j)=the assigned value of the pixels i through j.
$x_i$=the x coordinate of the pixels i through n.
$y_j$=the y coordinate of the pixels j through m.

The x and y spatial coordinates generated by the detector 54 are provided to an interface controller 56. The interface controller 56 maps the x and y spatial coordinates generated by the detector to corresponding pixel locations on the monitor 18. The interface controller 56 is coupled to a graphic overlay processor 58 and a robot controller 60. The graphic overlay processor 58 is coupled to the monitor 18. Although separate controllers are shown and described, it is to be understood that the blocks depicted are merely functional and that the operations may be performed by a single microprocessor or different combinations of processors.

Figure 4:
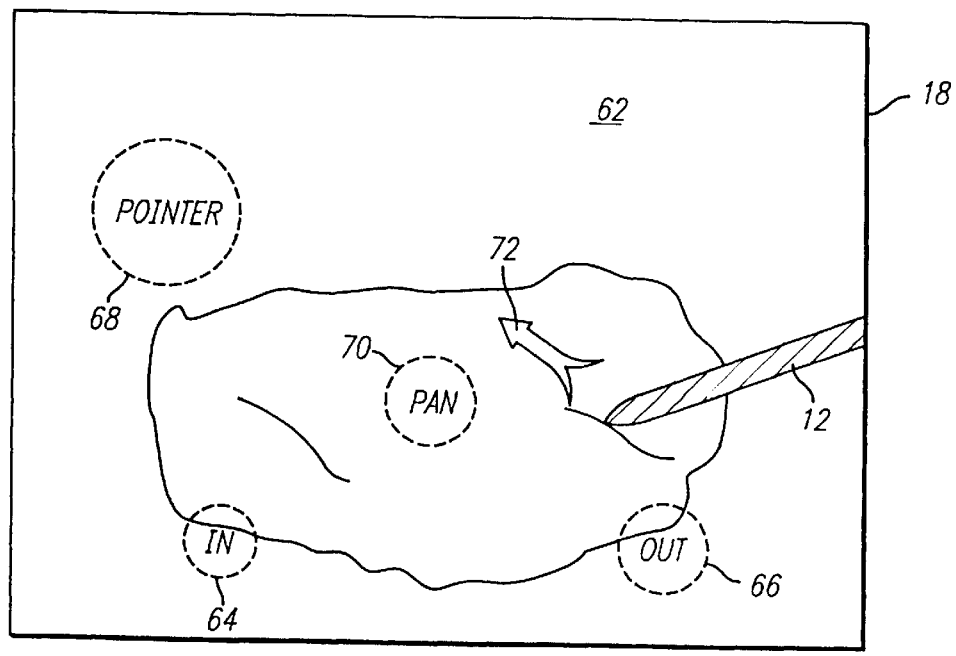
FIG. 4 is a front view of a monitor which displays a video image and a plurality of graphical overlays.

As shown in FIG. 4, the monitor 18 displays a video image 62 provided by the camera 16 of the endoscope 12. The video image 62 is typically an internal organ of a patient. The graphic overlay processor 58 generates a series of static graphic images 64–70 that overlay onto the video image 62 displayed by the monitor 18. The overlay processor 58 also generates a dynamic graphic cursor 72 that can move across the monitor 18. The graphic cursor 72 may move in conjunction with any movement of the laser beam 42 emitted from the pointer 40 mounted to the surgeon's head.

To move the cursor 72, the surgeon may move his head and vary the spatial location of the pointer signal 42 on the screen 48. The new pointer location is detected by the CCD camera 50. The position detector 54 computes the x and y spatial coordinates which are then provided to the interface controller 56. The interface controller 56 maps the new x and y spatial coordinates to pixel locations on the video image 62. The controller 56 then provides the new pixel locations to the graphic overlay processor 58 which displays the cursor 72.

The interface controller 56 may also generate output signals to move the robotic arm assembly 20 in conjunction with the position of the cursor 72. For example, the interface controller 56 may generate output signals to move the robotic arm 20 and endoscope 12 and to move the video image in the direction of the cursor. In this manner, the surgeon can view a new location within the patient by merely moving his head. Although a cursor 72 is shown and described, it is to be understood that the surgeon may move the robotic arm 20 and the video image 62 without a cursor 72 by merely tilting his head and watching the displayed image on the monitor 18.

The static graphic images 64–70 may provide input commands to control various devices such as the robotic arm assembly 20. For example, the graphic images 64 and 66 may provide ZOOM IN and ZOOM OUT commands for the video image. When the surgeon moves the cursor 72 into the area of the IN graphic image 64, the interface controller 56 generates output signals to move the robotic arm 20 so that the end of the endoscope moves closer to the object displayed by the monitor 18. Likewise, when the cursor 72 is moved into the OUT graphic 66, the controller 56 generates output signals to move the robotic arm 20 so that the endoscope moves away from the object shown on the monitor 18.

To determine the interaction between the cursor 72 and the graphic images 64–70, the interface controller 56 compares the pixel locations that correspond to the x and y coordinates provided by the detector 54 with a group of pixel locations associated with each graphic image. If the x and y pixel locations associated with the pointer signal equal a pixel location of a graphic image, the controller 56 generates a command associated with the graphic image. The graphic images 64–70 may be removed from the video image by drawing in air on the tube 46 and turning off the laser pointer 40.

The graphical image 68 may generate a command to create a "pointer" out of the cursor 72 so that any subsequent movement of the cursor 72 will not generate a corresponding movement of the robotic arm 20. The surgeon may use the "pointer as an instructional aid for other personnel viewing the monitor 18.

The robotic arm 20 can be manipulated by initially placing the cursor 72 in the PAN graphic 70 and then moving the cursor 72 about the monitor 18. The interface controller 56 generates new pixel locations associated with the cursor movement which are then provided to the robot controller 60 to move the robotic arm so that the video image moves in conjunction with the movement of the cursor and the spatial location of the laser beam on the screen.

Figure 5:
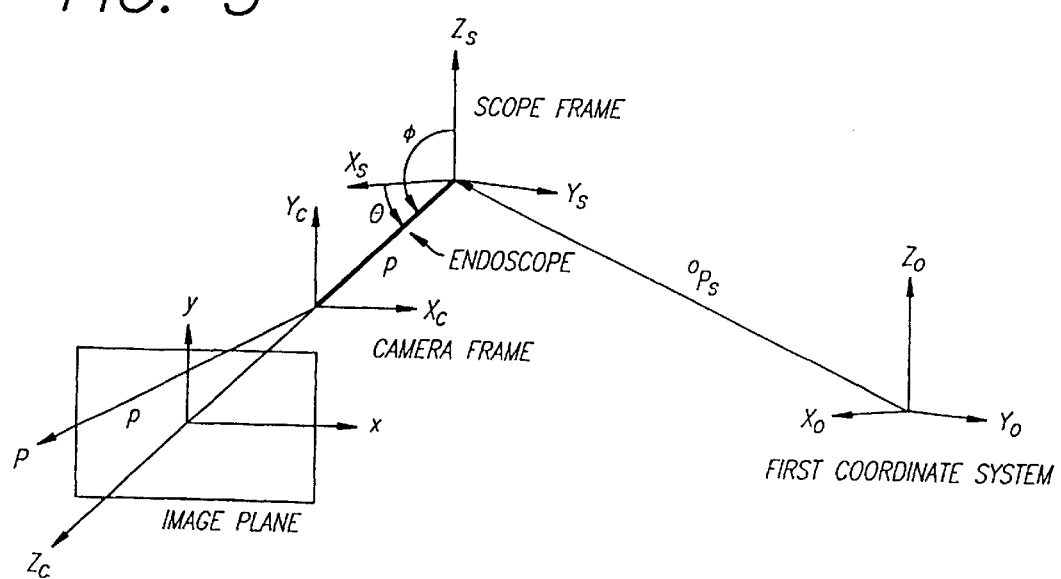
FIG. 5 is a schematic of an endoscope within various coordinate frames.

The process of moving the endoscope is performed by initially subtracting the new pixel position from an arbitrary reference pixel position to determine a $\Delta x$ and a $\Delta y$ pixel movement of the cursor 72 within the video image 62. The computed movement ($\Delta x$ and $\Delta y$) is multiplied by a weighted pseudoinverse of the following Jacobean matrix with reference to the coordinate system shown in FIG. 5.

$$\begin{bmatrix} \dfrac{-xy\sin\phi}{f} + y\cos\theta & \dfrac{-f\rho}{Z_c} - \left(f + \dfrac{x^2}{f}\right) & \dfrac{x}{Z_c} \\ -x\cos\theta - \sin\phi\left(f + \dfrac{y^2}{f_c}\right) - \dfrac{f\rho\sin\phi}{Z_c} & -\dfrac{xy}{f} & \dfrac{y}{Z_c} \end{bmatrix}$$

where;
the angles $\theta$, $\phi$ and $\rho$ are measured by robotic position sensors (not shown). The angles provide spherical coordinates of the endoscope within a scope frame coordinate system that has an origin at the pivot point of the instrument and the patient.
x, y=the new pixel coordinates of the reference point.
$Z_c$=is a constant.
f=the focal length of the endoscope lens.

The product ($V\theta$, $V\phi$ and $V\rho$) of the reference point movement ($\Delta x$ and $\Delta y$) and the Jacobean matrix is the computed movement of the endoscope by the robotic arm assembly in a spherical coordinate frame. The spherical coordinates ($V\theta$, $V\phi$ and $V\rho$) are converted into Cartesian coordinates (Vx, Vy and Vz) by a transformation. The movement of the endoscope within the scope frame is converted to the fixed first coordinate system by an additional transformation matrix or matrices.

Figure 6:
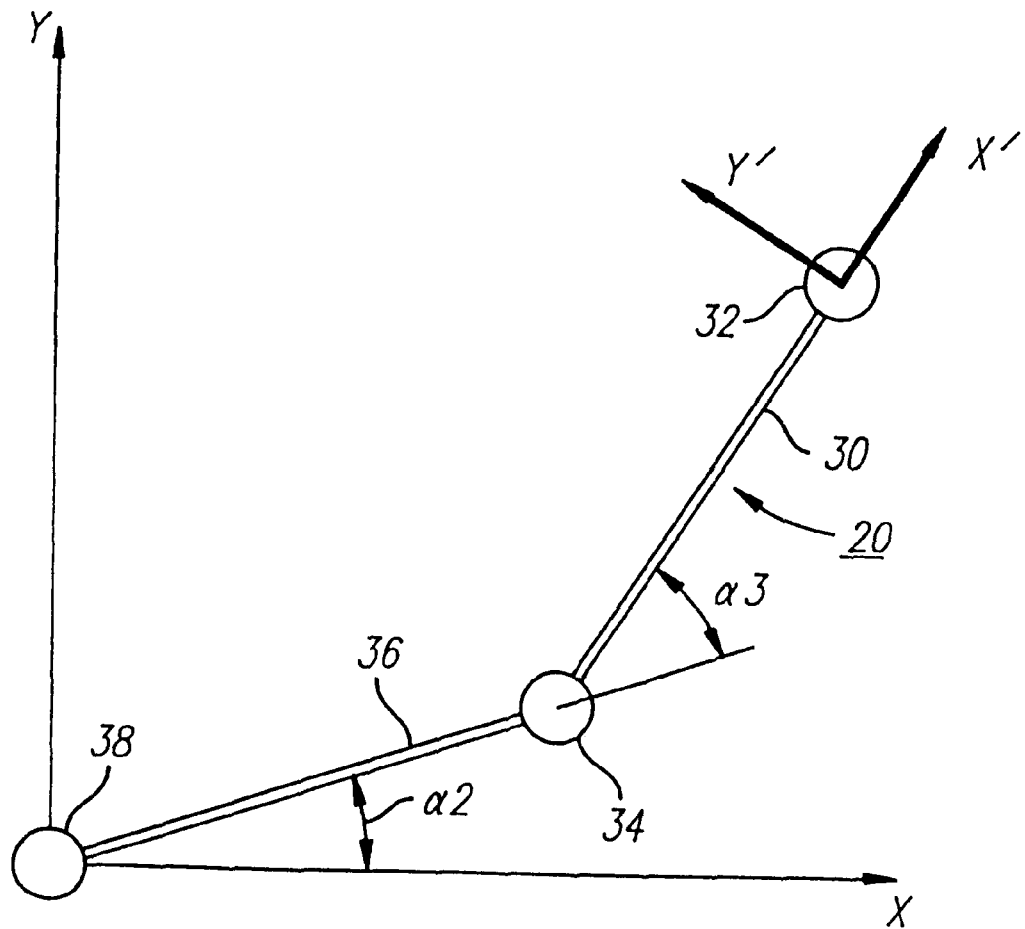
FIG. 6 is a schematic of a robotic arm.

Referring to FIG. 6, the controller 60 typically computes the movement of the robotic arm assembly 20 in accordance with the following equations.

$$a3 = \pi - \cos^{-1}\left(\dfrac{x^2 + y^2 - L1^2 + L2^2}{-2 \cdot L1L2}\right)$$

$$\Delta = \cos^{-1}\left(\dfrac{x^2 + y^2 + L1^2 - L1^2}{2L1\sqrt{x^2 + y^2}}\right)$$

$$a0 = \tan^{-1} 2\left(\dfrac{y}{x}\right)$$

$$a2 = a0 + / -\Delta$$

where;
a2=angle between the second linkage arm 36 and the x axis.
a3=angle between the first linkage arm 30 and the longitudinal axis of the second linkage arm 36.
L1=length of the second linkage arm.
L2=length of the first linkage arm.
x=x coordinate of the end effector in the first coordinate system.
y=y coordinate of the end effector in the first coordinate system.
To move the end effector to a new location of the x-y plane, the computer computes a change in the angles a2 and a3, and then provides output signals to move the actuators accordingly. The original angular position of the end effector is provided to the computer by the position sensors. The computer moves the linkage arms an angle that corresponds to the difference between the new location and the original location of the end effector. A differential angle $\Delta a2$ corresponds to the amount of angular displacement provided by the third actuator 38 and a differential angle $\Delta a3$ corresponds to the amount of angular displacement provided by the second actuator 34.

To improve the effectiveness of the system 10, the system is constructed so that the desired movement of the surgical instrument correlates to a direction relative to the image displayed by the monitor. Thus when the robotic arm moves the endoscope 12 up, the scope always appears to move in the up direction relative to the image displayed by the monitor. To accomplish this result, the computer converts the desired movement of the end of the endoscope in the third coordinate system to coordinates in the second coordinate system, and then converts the coordinates of the second coordinate system into the coordinates of the first coordinate system.

Referring to FIG. 2, the desired movement of the endoscope is converted from the third coordinate system to second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a6) & \cos(a5)\cos(a6) \end{pmatrix} \begin{pmatrix} \Delta x'' \\ \Delta y'' \\ \Delta z'' \end{pmatrix}$$

where;
$\Delta x''$=the desired incremental movement of the scope along the x" axis of the third coordinate system.
$\Delta y''$=the desired incremental movement of the scope along the y" axis of the third coordinate system.
$\Delta z''$=the desired incremental movement of the scope along the z" axis of the third coordinate system.
a5=the angle between the z' axis and the scope in the y'-z' plane.
a6=the angle between the z' axis and the scope in the x'-z' plane.
$\Delta x'$=the computed incremental movement of the scope along the x' axis of the second coordinate system.
$\Delta y'$=the computed incremental movement of the scope along the y' axis of the second coordinate system.
$\Delta z'$=the computed incremental movement of the scope along the z' axis of the second coordinate system.
The angles a5 and a6 are provided by position sensors coupled on the end effector 32.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix}$$

where;
$\Delta x'$=the computed incremental movement of the scope along the x' axis of the second coordinate system.
$\Delta y'$=the computed incremental movement of the scope along the y' axis of the second coordinate system.
$\Delta z'$=the computed incremental movement of the scope along the z' axis of the second coordinate system.
$\pi$=is the angle between the first linkage arm and the x axis of the first coordinate system.
$\Delta x$=the computed incremental movement of the scope along the x axis of the first coordinate system.
$\Delta y$=the computed incremental movement of the scope along the y axis of the first coordinate system.
$\Delta z$=the computed incremental movement of the scope along the z axis of the first coordinate system.

The incremental movements Δx and Δy are inserted into the algorithms described above for computing the angular movements (Δa2 and Δa3) of the robotic arm assembly to determine the amount of rotation that is to be provided by each actuator. The value Δz is used to determine the amount of linear movement provided by the linear actuator 24.

The endoscope 12 is typically coupled to the camera 16 such that any spinning of the instrument about its own longitudinal axis will result in a corresponding rotation of the video image 62 on the monitor 18. Rotation of the instrument and video image may disorient the viewer. It is therefore desirable to maintain the orientation of the video image. In the preferred embodiment, the end effector has a worm gear which rotates the surgical instrument about the longitudinal axis of the instrument. To insure proper orientation of the endoscope, the worm gear rotates the instrument about its longitudinal axis an amount Δθ6 to insure that the y" axis is oriented in the most vertical direction within the fixed coordinate system. Δθ6 is computed from the following cross-products.

$$\Delta\theta 6 = zi'' \times (yo'' \times yi'')$$

where;

Δθ6=the angle that the instrument is to be rotated about the z" axis.

yo"=is the vector orientation of the y" axis when the instrument is in the first position.

yi"=is the vector orientation of the y" axis when the instrument is in the second position.

zi"=is the vector orientation of the z" axis when the instrument is in the second position.

The vectors of the yi" and zi" axis are computed with the following algorithms.

$$[zi''] = a5 \begin{bmatrix} \cos a6 & 0 & -\sin a6 \\ -\sin a5 \sin a6 & \cos a5 & -\sin a5 \cos a6 \\ \cos a5 \sin a6 & \sin a5 & \cos a5 \cos a6 \end{bmatrix} \begin{bmatrix} 0 \\ 0 \\ 1 \end{bmatrix}$$

$$xi'' = z \times zi''$$

$$yi'' = zi'' \times xi''$$

where;

a6=is the angle between the instrument and the z axis in the y-z plane.

a5=is the angle between the instrument and the z axis in the x-z plane.

z=is the unit vector of the z axis in the first coordinate system.

The angles a5 and a6 are provided by the joint position sensors of the end effector. The vector yo" is computed using the angles a5 and a6 of the instrument in the original or first position. For the computation of yi", the angles a5 and a6 of the second position are used in the transformation matrix. After each arm movement yo" is set to yi" and a new yi" vector and corresponding Δθ6 angle are computed and used to re-orient the endoscope. Using the above described algorithms, the worm gear continuously rotates the instrument about its longitudinal axis to insure that the pivotal movement of the endoscope does not cause a corresponding rotation of the viewing image.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although graphic images which provide commands to control a robotic arm are shown and described, it is to be understood that the graphics may generate commands that control other devices. The graphic overlay processor 58 may provide an entire menu that allows the surgeon to adjust the operating table or the lighting of the camera 16. Additionally, surgical instruments such as laser cutters or electrode coagulators may be controlled by the surgeon through the head activated graphical interface provided by the present invention. The present invention generally provides a remotely controlled graphically based interface that allows the surgeon to control various devices and conditions at a surgical site.

We claim:

1. A system that allows a user to control a movement of a surgical instrument, wherein the surgical instrument is coupled to a display device that displays a video image of an object, comprising:

a mechanism that moves the surgical instrument;

a graphic overlay processor which overlays a dynamic graphic cursor onto the video image;

an input device that allows the user to move said dynamic graphic cursor in a first direction;

an interface controller that provides an output signal when said dynamic graphic cursor is moved in the first direction; and, a robot controller that receives said output signal from said interface controller and moves said mechanism so that the video image moves in the first direction.

2. The system as recited in claim 1, wherein said robot controller computes a movement of said mechanism based on said output signal of said interface controller and an original position of said mechanism so that the surgical instrument moves in a desired direction associated with the first direction, said robot controller provides output signals to said mechanism to move said mechanism so that the surgical instrument always moves in the desired direction.

3. The system as recited in claim 1, wherein an intersection of said mechanism and the surgical instrument defines an origin for a second coordinate system with respect to a first coordinate system, wherein the second coordinate system has a y-z plane, and said robot controller computes a movement of said mechanism from said output signal of said interface controller and provides output signals to said mechanism to move the surgical instrument so that a longitudinal axis of the surgical instrument always remains in the y-z plane.

4. The system as recited in claim 1, wherein said mechanism includes an end effector that holds the surgical instrument, said mechanism being located within a first coordinate system which has a first x axis, a first y axis and a first z axis, said end effector being located within a second coordinate system which has a second x axis, a second y axis and a second z axis, the surgical instrument is located within a third coordinate system which has a third x axis, a third y axis and a third z axis, said output signal of said interface controller correlates to a moving distance of the surgical instrument in the third coordinate system, said robot controller computes a moving distance of the surgical instrument in the second coordinate system from the moving distance within the third coordinate system, and computes a moving distance of the surgical instrument in the first coordinate system from the computed moving distance within the second coordinate system, and provides output signals to move said mechanism the computed moving distance within the first coordinate system.

5. The system as recited in claim 1, wherein said dynamic graphic cursor can be moved into a static graphic image to select a command.

6. The system as recited in claim 5, wherein said command moves said mechanism.

* * * * *